United States Patent [19]
Hitz et al.

[11] Patent Number: 5,151,522

[45] Date of Patent: Sep. 29, 1992

[54] PROCESS FOR PREPARING POLYCARBOXYLIC ACID IMIDAZOLINES BY CONDENSATION REACTION

[75] Inventors: Hans Hitz; Rolf Schaefer, both of Arisdorf, Switzerland; Heinrich Baust, Plankstadt; Wolfgang Gross, Mutterstadt, both of Fed. Rep. of Germany

[73] Assignees: Chemisches Institut Schaefer AG, Bubendorf, Switzerland; Joh. A. Benckiser GmbH, Ludwigshafen, Fed. Rep. of Germany

[21] Appl. No.: 733,851

[22] Filed: Jul. 22, 1991

Related U.S. Application Data

[62] Division of Ser. No. 535,135, Jun. 8, 1990, Pat. No. 5,049,315.

[30] Foreign Application Priority Data

Jun. 19, 1989 [DE] Fed. Rep. of Germany ....... 3919863

[51] Int. Cl.$^5$ ............................................ C07D 233/02
[52] U.S. Cl. .................................... 548/112; 548/300
[58] Field of Search ................................ 548/112, 300

[56] References Cited

U.S. PATENT DOCUMENTS

| | | | |
|---|---|---|---|
| 4,362,737 | 12/1982 | Schaefer et al. | 514/120 |
| 4,529,803 | 7/1985 | Tomalia et al. | 548/354 |
| 4,544,756 | 10/1985 | Patel | 548/354 |

FOREIGN PATENT DOCUMENTS

| | | |
|---|---|---|
| 1024972 | 2/1958 | Fed. Rep. of Germany. |
| 3137044 | 3/1983 | Fed. Rep. of Germany. |

OTHER PUBLICATIONS

B. R. Bluestein et al., "Amphoteric Surfactants", New York, pp. 14-18, 23-29, 42-47 (1982).
H. Hitz et al., "Amphoteric Imidazolinium Surfactant with High Content of Imidazoline Ring," Parfuemerie und Kosmetik, 64, Jan., Nr. 1/83.

Primary Examiner—Patricia L. Morris
Assistant Examiner—Lenora A. Miltenberger
Attorney, Agent, or Firm—Foley & Lardner

[57] ABSTRACT

The present invention provides a process for preparing polycarboxylic acid imidazolines of the general formula:

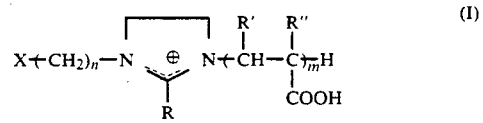

wherein X is —Cl, —OH, —O—SO$_3$H, —O—PO$_3$H$_2$, —O—CH$_2$—CH$_2$—COOH, —NH$_2$, —NHalk or —N(alk)$_2$, alk being an alkyl radical containing up to 6 carbon atoms, n is a whole number of from 2 to 4, R is a C$_8$-C$_{18}$ hydrocarbon radical which is straight-chained, branched, saturated or one to three times unsaturated, m is a whole number of from 2 to 5, R' is a hydrogen atom or a carboxyl group and R" is a hydrogen atom or a methyl radical. In the process, a compound of the formula

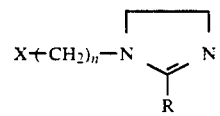

in which R, X and n are as defined above, is condensed with about a 2- to 5-fold excess of acrylic acid, methacrylic acid, maleic acid or a mixture thereof.

3 Claims, No Drawings

PROCESS FOR PREPARING POLYCARBOXYLIC ACID IMIDAZOLINES BY CONDENSATION REACTION

This application is a division of application Ser. No. 07/535,135, filed Jun. 8, 1990 now U.S. Pat. No. 5,049,315.

BACKGROUND OF THE INVENTION

The present invention is concerned with new polycarboxylic acid imidazolines, a process for the preparation thereof and cleaning agents containing them.

Cleaning agents, especially agents for washing the body and hair, as well as textile and dish washing agents but also industrial cleaning agents, are generally mixtures of tensides and tenside adjuvants. The tensides used for this purpose, as well as mixtures thereof with one another, consist of anionic, neutral, amphoteric and/or cationic surface-active materials. These surface-active materials contain a hydrophobic part, which consists of hydrocarbons, as well as a hydrophilic or polar part.

In the case of anionic tensides, the hydrophilic part consists of a negatively charged grouping, this being a sulfate, sulfonate, phosphate, phosphonate or carboxylate. These groupings can, however, also be attached to the hydrocarbon chains via a polyoxyethylene chain. Whereas the sulfonate- and sulfate-containing hydrocarbons are strongly anionically charged tensides, the phosphates, phosphonates and carboxylates are weakly anionic tensides.

In the case of the neutral tensides, the hydrophilic part consists of a polar, neutral grouping, for example of amine oxides, polyoxyethyl radicals, carbohydrates or polyoxyethylated carbohydrates.

In the case of the amphoteric tensides, the polar groups are zwitterions, i.e. these groups contain not only positive but also negative charges. These include especially betaines and protein condensates, as well as taurates.

In the case of the cationic tensides, the polar groups consist of mono-, di-, tri- and quaternary-substituted amines, all of which are positively charged in the neutral pH range. Whereas the mono-, di- and tri-substituted amines are weakly cationic tensides, the quaternary-substituted amines are strongly cationic.

The above-described tensides and mixtures thereof are problematical with regard to biological systems: in the case of tenside mixtures in the field of body cleansing agents, contact results between the formulation and the surface of the skin. Such tenside-containing mixtures can bind strongly or less strongly to the surface of the skin and have a negative influence on the microbial skin flora, which is the natural immunity system of the skin.

The exchange action of the tensides with the microbial skin flora can result in changes thereof and weaken them and, as a consequence, provide a point of attack for infections by foreign microbes and fungi. As a result thereof, allergies and dermatoses can manifest themselves, a fact which today is observed to an increasing extent.

In the case of the exchange action of the tensides with the skin, in many cases it can result in desiccation and desquamation and, after chronic exchange action, in microlesions.

After the cleaning of textiles, as well as of solid surfaces, which leave behind tenside-containing waste water, an exchange action results between the tensides and the micro-organisms of the waste water disposal plant, in which case these tensides can impair or destroy the viability of the microflora which break down materials.

Thus, tensides often act as true cell poisons. This applies to the strongly anionic and especially to the strongly cationic tensides.

Therefore, attempts have been made, by means of special mixtures of the described tensides with one another to obtain formulations which reduce the toxicity with regard to the aggressiveness of the strongly anionic, as well as of the strongly cationic tensides, i.e. to detoxify them.

This was achieved by the selection of favourable formulation ratios of neutral and amphoteric tensides with anionic tensides. The anionic tensides, especially the alkyl sulfates and the alkyl ether sulfates, are the most used surface-active materials in today's cleaning and care agents.

However, this detoxification is relative, i.e. the strongly anionic and the strongly cationic tensides can only be detoxified by up to a certain percentage.

Such relatively detoxified tensides are referred to as mild formulations.

The residual aggressiveness of the mild tenside formulations described in the prior art also manifests itself in that, in the case of contact of these materials with the cornea and mucosa of the eye, in normal cases, a strong burning sensation is experienced which can proceed as far as a true irritation of the eye.

Recently, attention has also been drawn to the problems of traces of such tenside-containing mixtures: in the case of oxyethylated products dioxans are formed as synthesis by-products, in the case of amines nitrosamines are formed and in the case of sulfates sulfones are formed, all of which are highly toxic or are potentially carcinogenic.

From H. Hitz et al., Parfumerie und Kosmetik, 64 16–21/1983, a new group of 2-alkylimidazolineN-propionic acids (amphonyls) is known which are milder tensides than other amphoteric compounds. However, they give rise to considerable formulation problems since they are substantially very poor viscosity increasing materials and hydrolyse in alkaline media with cleavage of the imidazole ring.

SUMMARY OF THE INVENTION

Accordingly, it is an object of the present invention to provide new and highly effective tensides which, alone or in admixture with other tensides, are nonaggressive or only slightly aggressive.

Another object of the present invention is to provide improved tensides which can be broken down biologically and which are stable in acidic and alkaline media.

A further object of the present invention is to provide a process for producing the foregoing tensides.

In accomplishing the foregoing objectives, there has been provided, in accordance with one aspect of the present invention, a polycarboxylic acid imidazoline of the general formula:

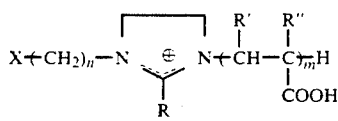

(I)

in which
X is —Cl, —OH, —OSO$_3$H, —OPO$_3$H$_2$, —O—CH$_2$—CH$_2$—COOH, —NH$_2$, —NH(alk) or —N(alk)$_2$,
alk is an alkyl radical containing 1 to 6 carbon atoms,
n is a whole number from 2 to 4,
m is a whole number from 2 to 5,
R is a C$_{8-18}$ hydrocarbon chain which is straight-chain or branched, and saturated or 1 to 3 times unsaturated,
R' is H or a carboxyl group, and
R" is H or —CH$_3$ In accordance with another aspect of the present invention there is provided a process for preparing a compound as described above, which comprises the step of condensing a compound of the general formula

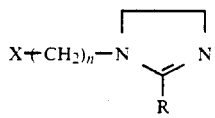

(II)

in which R, X and n have the meanings defined above, with about a 2- to 5-fold excess of acrylic acid, methacrylic acid, maleic acid, an active derivative thereof or a mixture thereof.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Suprisingly, in the case of a comparatively large excess of the unsaturated carboxylic acid, a polymerization in the carboxylic acid side chain is observed whereas according to the previous literature (v. supra) a derivatization of the substituent X was to have been expected.

The condensation is preferably carried out in a melt of the components at a temperature of from about 100° to 150° C. but, for simplification of the mixing, an inert solvent, for example toluene or xylene or a high boiling point paraffin, can also be added thereto.

The reaction thereby does not result in a uniform product but rather in a mixture of compounds of differing chain length m, in which case, depending upon the excess of carboxylic acid, m reaches a maximum of 2 to 4.

A chromatographic separation of the reaction components is possible, for example with anion exchangers, but this is not necessary for the use of the compounds as tensides. Therefore, for economic reasons, the resultant mixture is preferably used directly.

The starting materials of general formula (II) are known or can be obtained in known manner by the condensation of compounds of the general formula:

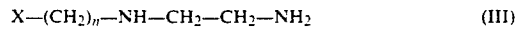

(III)

in which X and n have the above-given meanings, with fatty acids or fatty acid esters of the general formula:

(IV)

in which R has the above-given meaning and Y is a hydrogen atom or an alkyl radical, with the splitting off of alcohol or water. The naturally-occurring triglycerides are also preferably used.

In the case of the use of these new polycarboxylic acid imidazolines alone or in admixture with other tensides, we have, surprisingly, now found that it is possible to produce pH stable and very mild tenside formulations.

Thus, according to the present invention, there are also provided cleaning and care agents containing at least one anionic, non-ionic, cationic and/or amphoteric tenside and at least one polycarboxylic acid imidazoline according to the present invention, the ratio of tenside to imidazoline preferably being from about 2:98 to 50:50 and more preferably from 10:90 to 20:80.

In the field of body care agents, ultramild formulations can be produced with the use of the compounds of general formula (I), in which case sulfates, ether sulfates, alkyl sulfates and alkyl sulfonates are omitted because of the extremely high toxicity thereof. At the same time, problems due to traces can be eliminated.

In particular, the properties of the ultramild tenside formulations, according to the invention, for the whole field of body care agents and cleaning agents were tested and confirmed on biological models, as well as on humans.

The following biological test models were used:
1. the eye and eye mucosa compatibility
2. the comfort test on the human eye
3. the dermal compatibility on rabbits
4. the During chamber test on humans
5. the inhibition of proteolytic activity by means of trypsin
6. the contact allergenic properties on guinea pigs
7. the nutrition test which describes the compatibility of the human skin flora with the formulations.

The nutrition test is a process in which the primary and secondary toxicity on micro-organisms of a material or material mixture (in the present case tenside formulations) are determined. In the case of body care agents, as micro-organisms there are used the various natural microbes which are present on human skin. In the case of tenside mixtures in waste water, as biological models there are used the microflora of the waste water treatment plants.

In the tests, the above-mentioned bacteria are suspended in a carbon-free medium. Thereafter, as the source of carbon, there is added to the suspension the substance to be tested (in this case a tenside or tenside formulation). On the basis of the growth curves of the microbes, the primary and secondary toxicity of the material to be tested can be exactly determined.

The ultramild formulation of a shower gel described in the following Example 11 has, in comparison with the commercially available typical so-called mild baby shampoos (prior art), given the following results:

|  | formulation (Example 11) irritation index | baby shampoo (prior art) irritation index |
|---|---|---|
| eye and mucous membrane compatibility (draize, formulation diluted 1:5 with water, eye unrinsed) | 0.00 | 2.17 |
| comfort test on the human eye (formulation diluted 1:200) | 1.1 | 2.6 |
| dermal compatibility on rabbits (formulation diluted 1:5) | 1.7 | 2.7 |
| During chamber test on humans (formulation diluted 1:2.5) | 5 | 26 |
| inhibition of the proteolytic activity of trypsin (threshold concentration of the wash-active substance (WAS) in percent) | 7.5% | 4% |
| nutrition test (formulation diluted 1:20) cell division rate of the human skin flora (10% growth in hours) | 47 h. | 172 h. |

From the above-described results, it can be seen that the formulations according to the present invention can, in all biological models, be described as being ultramild in comparison with the prior art when it is borne in mind that the prior art is a mild formulation.

The following Examples are given for the purpose of illustrating the present invention:

EXAMPLE 1

Aminoethylethanolamine (1.2 mole) is stirred with maize germ oil ($\frac{1}{3}$ mole of triglycerides) at 190° C. for 2 hours under normal pressure. Subsequently, the pressure is lowered to 10 mbar and the excess aminoethylethanolamine (20%) and the resultant glycerol thereby removed over the course of 2 hours from the reaction mixture by distillation. The alkylimidazolinium base (1 mole) resulting in the reaction vessel is cooled to 140° C. At this temperature, acrylic acid (2.2 mole) is added to the imidazolinium base over the course of 2 hours and stirring is continued for a further 2 hours at the same temperature. Thereafter, the reaction product is cooled to 90° C., diluted with 1.5 parts by weight of water and titrated with 10N aqueous sodium hydroxide solution to pH 5 ($R=C_{18:1}-C_{18:3}$, $n=2$, $m=2-5$, $R'$, $R''=H$, $X=OH$). The approximate composition of the product is 2% imidazoline, 5% imidazoline-propionic acid, 82% imidazoline dipropionic acid, 8% imidazoline tripropionic acid, 3% imidazoline polypropionic acid.

EXAMPLE 2

Analogous to Example 1 but coconut oil is used instead of maize germ oil ($R=C_{14}$, $n=2$, $m=2-5$, $R'$, $R''=H$, $X=OH$).

EXAMPLE 3

Analogous to Example 1 but coconut forerunning fatty acid triglyceride is used instead of maize germ oil ($R=C_8-C_{10}$, $X=-OH$).

EXAMPLE 4

Analogous to Example 1 but chloroethylethylenediamine is used instead of aminoethylethanolamine ($n=2$, $X=Cl$).

EXAMPLE 5

Analogous to Example 1 but sulfatidylethylethylenediamine is used instead of aminoethylethanolamine ($n=2$, $X=-OSO_3H$).

EXAMPLE 6

Analogous to Example 1 but phosphatidylethylethylenediamine is used instead of aminoethylethanolamine ($n=2$, $X=-OPO_3H_2$).

EXAMPLE 7

Analogous to Example 1 but ethylenediaminoethoxypropionic acid is used instead of aminoethylethanolamine ($n=2$, $X=-O-CH_2-CH_2-COOH$).

EXAMPLE 8

Analogous to Example 1 but diethylenetriamine monohydrochloride is used instead of aminoethylethanolamine.

EXAMPLE 9

Analogous to Example 1 but oleylaminoethylethylenediamine is used instead of aminoethylethanolamine.

EXAMPLE 10

Analogous to Example 1 but distearylaminoethylethylenediamine is used instead of aminoethylethanolamine.

EXAMPLE 11

Shower gel

| mixture according to Example 2 (40%) | 7.5 parts |
|---|---|
| cocoyl sulfosuccinate (30%) | 15 parts |
| cocoamidopropylbetaine (30%) | 20 parts |
| stearyl monoglyceride (20%) | 1 part |
| protein hydrolysate (100%) | 0.2 part |
| lauryl alcohol decaethoxylate (100%) | 0.2 part |
| water ad | 100 parts |

EXAMPLE 12

Conditioner shampoo/baby shampoo

| mixture according to Example 1 (40%) | 7.5 parts |
|---|---|
| cocoyl sulfosuccinate (30%) | 15 parts |
| cocoamidopropylbetaine (30%) | 20 parts |
| stearyl monoglyceride (20%) | 1 part |
| protein hydrolysate (100%) | 0.2 part |
| lauryl alcohol decaethoxylate (100%) | 0.2 part |
| water ad | 100 parts |

EXAMPLE 13

Foam bath

| mixture according to Example 2 (40%) | 7.5 parts |
|---|---|
| cocoyl sulfosuccinate (30%) | 15 parts |
| cocoamidopropylbetaine (30%) | 20 parts |
| lauryl monoglyceride (20%) | 1 part |
| protein hydrolysate (100%) | 0.2 part |

EXAMPLE 14

Face cleansing lotion

| | |
|---|---|
| mixture according to Example 2 (40%) | 27.5 parts |
| cocoyl sulfosuccinate (30%) | 15 parts |
| stearyl monoglyceride (20%) | 1 part |
| protein hydrolysate (100%) | 0.2 part |
| lauryl alcohol decaethoxylate (100%) | 0.2 part |
| water ad | 100 parts |

EXAMPLE 15

Cream bath/oil bath

| | |
|---|---|
| mixture according to Example 2 | 10 parts |
| lauryl alcohol octaethoxylate | 10 parts |
| lauryl alcohol decaoxyethyl carboxylate | 5 parts |
| oleyl alcohol | 20 parts |
| wheat germ oil | 20 parts |
| maize germ oil | 27 parts |
| lanolin alcohol | 8 parts |

EXAMPLE 16

Conditioner emulsion

| | |
|---|---|
| mixture according to Example 1 | 3 parts |
| vaseline oil | 6 parts |
| PEG 20 oleate | 5 parts |
| propylene glycol | 5.5 parts |
| collgen (10%) | 2 parts |
| Hypericum extracts | 0.9 part |
| water ad | 100 parts |

EXAMPLE 17

Liquid soap

| | |
|---|---|
| mixture according to Example 2 | 8 parts |
| ethoxylated glyceryl monolaurate | 1 part |
| lauryl ether sulfate (28%) | 40 parts |
| water ad | 100 parts |

EXAMPLE 18

Tablet soap

Natural soap

| | |
|---|---|
| mixture according to Example 2 | 5.5 parts |
| soap base mass, 80% total fatty acids | |
| sodium salt, tallow/coconut 80:20 | 90 parts |
| polyphosphates | 3 parts |
| titanium dioxide | 0.25 part |

EXAMPLE 19

Syndet soap

| | |
|---|---|
| mixture according to Example 2 | 9 parts |
| fatty $C_{12}$-$C_{18}$ alcohol sulfate | 30 parts |
| sodium salt | |
| polyphosphates | 3 parts |
| fatty alcohol sulfosuccinate | 20 parts |
| disodium salt | |
| starch | 18 parts |
| paraffin | 9 parts |
| stearyl alcohol | 6 parts |
| cetyl alcohol | 4 parts |

EXAMPLE 20

Hand rinsing agent

| | |
|---|---|
| mixture according to Example 1 | 5 parts |
| linear lauryl benzene sulfonate (100%) | 20 parts |
| protein hydrolysate | 0.5 part |
| water ad | 100 parts |

EXAMPLE 21

Dish washing machine agent (phosphate-free)

| | |
|---|---|
| mixture according to Example 3 | 5 parts |
| stearyl alcohol pentaethoxylate | 10 parts |
| lauryl trioxyethylcarboxylate (50%) | 3 parts |
| sodium metasilicate/sodium hydroxide | 5 parts |
| water ad | 100 parts |

EXAMPLE 22

Fine washing agent/wool washing agent

| | |
|---|---|
| mixture according to Example 2 | 4 parts |
| lauryl benzenesulfonate (100%) | 15 parts |
| lanolin alcohol | 15 parts |
| water ad | 100 parts |

EXAMPLE 23

All-purpose cleaner

| | |
|---|---|
| mixture according to Example 3 | 5 parts |
| secondary alkane sulfonate (100%) | 15 parts |
| potassium oleate (100%) | 0.5 part |
| sodium carbonate | 2 parts |
| trisodium citrate | 1 part |
| water ad | 100 parts |

EXAMPLE 24

Industrial detergent

| | |
|---|---|
| mixture according to Example 3 | 5 parts |
| lauryl benzenesulfonate | 10 parts |
| lauryl ether sulfate (28%) | 5 parts |
| water ad | 100 parts |

What is claimed is:

1. A process for preparing a polycarboxylic acid imidazoline compound of the formula

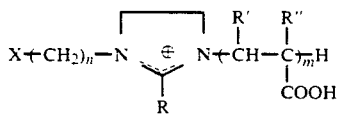

in which

X is —Cl, —OH, —OSO$_3$H, —OPO$_3$H$_2$, —O—CH$_2$—CH$_2$—COOH, —NH$_2$, —NH(alk) or —N(alk)$_2$, alk is an alkyl radical containing 1 to 6 carbon atoms, n is a whole number from 2 to 4, m is a whole number from 2 to 5, R is a C$_{8-18}$ hydrocarbon chain which is straightchain or branched, and saturated or 1 to 3 times unsaturated, R' is H or a carboxyl group, and R" is H or —CH$_3$, which comprises the step of condensing a compound of the general formula

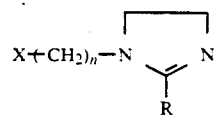

in which R, X and n are as defined above, with about a 2- to 5-fold excess of acrylic acid, methacrylic acid, maleic acid, or a mixture thereof.

2. A process as claimed in claim 1, wherein said condensation is carried out in a melt of the recited components at a temperature of about 100° to 150° C.

3. A process as claimed in claim 2, wherein an inert solvent is added to said components.

* * * * *